United States Patent [19]

Lewis et al.

[11] Patent Number: 5,879,534
[45] Date of Patent: Mar. 9, 1999

[54] NON-ENOLIZABLE OXYGENATES AS ANTI FOULANTS IN ETHYLENE DICHLORIDE MANUFACTURE

[75] Inventors: Vincent E. Lewis, Missouri City; Robert D. McClain; Michael K. Poindexter, both of Sugar Land, all of Tex.

[73] Assignee: Nalco/Exxon Energy Chemicals, L.P., Sugar Land, Tex.

[21] Appl. No.: 102,483

[22] Filed: Jun. 22, 1998

Related U.S. Application Data

[63] Continuation-in-part of Ser. No. 804,050, Feb. 21, 1997, Pat. No. 5,770,041.

[51] Int. Cl.$^6$ .................................................... C10G 9/16
[52] U.S. Cl. ................................. 208/48 AA; 208/48 R; 585/950; 203/6; 203/8
[58] Field of Search ........................... 208/48 AA, 48 R; 585/950; 203/6, 8; 570/117, 262, 264

[56] References Cited

U.S. PATENT DOCUMENTS

| | | |
|---|---|---|
| 3,024,277 | 3/1962 | Hotten . |
| 3,173,770 | 3/1965 | Thompson et al. . |
| 3,364,130 | 1/1968 | Barnum et al. . |
| 4,422,953 | 12/1983 | Grace et al. . |
| 4,673,489 | 6/1987 | Roling . |
| 4,952,301 | 8/1990 | Awbrey . |
| 5,110,997 | 5/1992 | Dickakian . |
| 5,160,425 | 11/1992 | Lewis . |
| 5,194,143 | 3/1993 | Roling . |
| 5,220,104 | 6/1993 | McDaniel . |
| 5,240,469 | 8/1993 | Poindexter . |
| 5,264,114 | 11/1993 | Dunbar . |
| 5,288,394 | 2/1994 | Lewis et al. . |
| 5,324,393 | 6/1994 | Poindexter . |
| 5,527,447 | 6/1996 | Roof . |
| 5,614,080 | 3/1997 | Roof . |
| 5,770,041 | 6/1998 | Lewis et al. .................. 208/48 AA |

*Primary Examiner*—Walter D. Griffin
*Attorney, Agent, or Firm*—Elaine M. Ramesh; Thomas M. Breininger

[57] ABSTRACT

A method of inhibiting the formation of fouling deposits occurring in spent caustic wash systems used for ethylene dichloride (EDC) manufacturing processes. Fouling occurs in these systems when they are in contact with EDC processing streams contaminated with oxygen-containing compounds, such as aldehydes. These deposits are formed in EDC processing streams contaminated with oxygen-containing compounds while in contact with a caustic solution having a pH>7. The invention comprises adding an effective deposit-inhibiting amount of a non-enolizable carbonyl compound to the caustic solution. Preferred non-enolizable carbonyl compounds are formaldehyde, glyoxal, benzaldehyde, p-anisaldehyde, formic acid, glyoxalic acid and paraformaldehyde.

7 Claims, No Drawings

NON-ENOLIZABLE OXYGENATES AS ANTI FOULANTS IN ETHYLENE DICHLORIDE MANUFACTURE

This application is a continuation-in-part of application Ser. No. 08/804,050 filed Feb. 21, 1997, now U.S. Pat. No. 5,770,041, entitled "Non-Enolizable Oxygenates as Antifoulants" by V. Lewis, M. Poindexter and R. McClain.

FIELD OF THE INVENTION

A method of inhibiting the formation of fouling deposits occurring in spent caustic wash systems used for ethylene dichloride manufacturing processes. Fouling occurs in these systems when they are in contact with EDC processing streams contaminated with oxygen-containing compounds, such as aldehydes. These deposits are formed in EDC processing streams contaminated with oxygen-containing compounds while in contact with a caustic solution having a pH>7. The invention comprises adding an effective deposit-inhibiting amount of a non-enolizable carbonyl compound to the caustic solution. Preferred non-enolizable carbonyl compounds are formaldehyde, glyoxal, benzaldehyde, p-anisaldehyde, formic acid, glyoxalic acid and paraformaldehyde.

BACKGROUND OF THE INVENTION

A major problem encountered in the treatment of various hydrocarbon charge stocks is the phenomenon recognized as and descriptively called fouling. This phenomenon is manifested in the form of deposits which frequently form on the metal surfaces of the processing equipment and tend to decrease the efficiency of the intermediate processing operations. The results of fouling appear in the form of heat transfer loss, increased pressure drop and a loss in throughput rate. Fouling also increases the safety risks associated with operating a chemical process. It is therefore a beneficial practice to inhibit the build-up of deposits in processing equipment that would otherwise reduce capacity and overall plant efficiency.

Ethylene dichloride (EDC) is produced by two methods; direct chlorination and oxychlorination. Both chlorination reactions are combined in most production plants to produce EDC by what is known as a balanced process. Hydrochloric acid produced in the direct chlorination process is used as a feedstock in the oxychlorination process.

Oxychlorination is a catalytic process by which ethylene, oxygen and hydrogen chloride are combined to produce ethylene dichloride and water. Any time ethylene, oxygen and a catalyst are combined, the possibility of oxidation exists. Acetaldehyde is an oxidation product of ethylene, and it is a minor by-product of the oxychlorination process.

From the reactor the effluent (crude EDC) is washed with water and caustic to remove as much hydrogen chloride as possible from the stream. It is during the caustic wash step that acetaldehyde undergoes a base-catalyzed polymerization.

Generally, the basic washing entails contacting the ethylene dichloride with an aqueous basic solution in a wash tower to remove hydrogen chloride therefrom. The conditions in the wash tower are conducive for condensation reactions of many enolizable aldehydes (such as acetaldehyde) contained therein.

The term "crude ethylene dichloride" refers to unpurified EDC which leaves the chlorination of oxychlorination units. Crude EDC also refers to the feed stream for the EDC Tar Still. These units may be considered distillation separation units which separate the crude EDC stream into an overhead stream of purified EDC and a bottoms stream of EDC, 1,1,2-trichloroethane, hexachloroethane, hexachlorobenzene, with fouling amounts of chlorinated or oxychlorinated polymeric material. The fouling in the bottoms is severe at EDC levels of below about 30 wt %, and particularly severe at EDC levels of below about 30 wt %, and particularly severe at EDC levels of 20 wt % or below. At high EDC levels in the bottoms, EDC acts as a solvent for the fouling materials.

Materials from the direct chlorination unit often contain not only chlorinated products, but also iron complexes; the iron typically comes from the catalyst (e.g. ferric chloride or tetrachloroferrate salts) used in the reaction or from corrosion of the equipment used in the process. These unwanted species, i.e. extraneous organic chloride/oxygenates and iron complexes, are typically removed through a series of aqueous washings and distillation columns. Columns are used to concentrate and remove the tars (i.e. heavies) formed either during the chlorination step or downstream of the reactors. Tars are generally high boiling polychlorinated by-products with poorly defined compositions. Material lighter than ethylene dichloride (b.p. 83° C.) is also removed through fractionation. After prolonged usage, both types of columns eventually foul due to the accumulation of non-volatile by-products.

Some of the by-products are likely due to unwanted oxidation (e.g. chloral and other oxygenated by-products are known to form). Oxygen is frequently an impurity in chlorine, and oxygen is also used in the oxychlorination process. Infrared analysis of non-volatile components from a heavy ends removal column has revealed that carbonyl moieties do indeed exist.

Serious fouling occurs in the various units handling the liquid EDC. For example, in the primary EDC Recovery Unit, fouling occurs in the distillation trays and the transfer facilities, particularly the retort furnace. EDC fouling is particularly serious in the liquid phase of EDC in the primary EDC Recovery Unit, the EDC Recovery Tar Still, and the EDC Recycle Tar Still.

It is not uncommon for these units to foul within periods of time as short as a few days. If it were possible, by the use of additives, to increase the time before fouling caused shut downs for cleaning a valuable contribution to the art would be made. Not only would run-length of the unit be increased, but there would be a reduction in waste and lower potential exposure to those who clean the unit.

Among the methods for inhibiting carbonyl fouling in caustic scrubbers are U.S. Pat. No. 4,673,489 wherein hydroxylamine and its hydrochloride and hydrogen sulfate salts have been used to inhibit polymer formation caused by condensation reactions of aldehydes contained in caustic scrubber units; U.S. Pat. No. 4,952,301 wherein ethylenediamines and water soluble salt forms thereof have been used to inhibit carbonyl based fouling, particularly aldehyde fouling, that often occurs during caustic scrubbing of liquid or gas phase hydrocarbon streams in the base wash unit; U.S. Pat. No. 5,264,114 wherein the use of amine compounds to inhibit the deposition of foulants during caustic washing is disclosed; U.S. Pat. No. 5,160,425 wherein carbohydrazide has been disclosed as useful for inhibiting polymeric fouling deposits during the caustic scrubbing of pyrolytically-produced hydrocarbons contaminated with oxygen-containing compounds in, hydrazides for the same purpose have been disclosed in U.S. Pat. No. 5,288,394; and U.S.

Pat. No. 5,194,143 wherein an acetoacetate ester is used in a method for inhibiting fouling during caustic washing of hydrocarbons. Amide condensation products of monocarboxylic acids and aliphatic polyamines for the same purpose were disclosed in U.S. Pat. No. 3,364,130. Additionally, U.S. Pat. No. 5,220,104 discloses the use of percarbonate salts for the same purpose. Yet none of these references disclose the novel treatment disclosed herein, and the majority would be unsuitable for the ethylene dichloride caustic tower environment.

Antifoulant dispersants have been described for the prevention of fouling in ethylene dichloride streams within the distillation units of the ethylene dichloride manufacturing process. For example, U.S. Pat. Nos. 5,240,469 and 5,324,393 disclose the use of a composition comprising an acrylate ester containing $C_4$–$C_{22}$ alcohol esters and amino alcohol esters, phenylene diamine and a heavy aromatic solvent; and U.S. Pat. No. 5,110,997 discloses use of an acylated amine, a magnesium sulfonate or a blend of both.

However, dispersants such as those described above as useful for distillation tower treatment would not also serve as antifoulants for caustic tower treatment. This is so because the caustic tower, treated by the antifoulants disclosed herein, is located in front of the distillation units in an ethylene dichloride manufacturing facility. The bottom of the caustic tower contains aqueous sodium hydroxide, and the overhead steam from the caustic tower contains water and crude ethylene dichloride. The caustic tower (also referred to as a spent caustic wash system) is an aqueous environment. This stream goes next to the distillation section, wherein water and light hydrocarbons are removed in the dehydration tower. The bottom of the distillation unit does not contain any water, but rather is organic in nature. Therefore the environment in the caustic tower is different than the environment within the distillation unit, and the ensuing problems and their solutions generated within the distillation tower will be different from those generated within the caustic tower.

Moreover, inhibition of corrosion in halocarbon systems with succinic acid derivatives is disclosed in U.S. Pat. No. 4,422,953. Since corrosion does not occur in caustic towers under normal operating conditions, corrosion inhibitors would not be used in the caustic towers of either ethylene plants or ethylene dichloride plants.

A method for inhibiting ethylene dichloride process stream fouling by preventing polymerization due to aldol condensation of aldehydes such as acetaldehyde that does not interfere with overall plant operations or in the operation of individual process units would therefore be a highly desirable advancement in the art of ethylene dichloride manufacture.

SUMMARY OF THE INVENTION

A method of inhibiting the formation of fouling deposits occurring in spent caustic wash systems used for ethylene dichloride manufacturing processes. Fouling occurs in these systems when they are in contact with EDC processing streams contaminated with oxygen-containing compounds, such as aldehydes. These deposits are formed in EDC processing streams contaminated with oxygen-containing compounds while in contact with a caustic solution having a pH>7. The invention comprises adding an effective deposit-inhibiting amount of a non-enolizable carbonyl compound to the caustic solution. Preferred non-enolizable carbonyl compounds are formaldehyde, glyoxal, benzaldehyde, p-anisaldehyde, formic acid, glyoxalic acid and paraformaldehyde.

DESCRIPTION OF THE INVENTION

The term deposits as utilized herein refers to polymeric residues which are due to oxygen-containing contaminants. Non-enolizable carbonyl compounds may be utilized for the inhibition of the formation of polymeric fouling deposits in caustic towers.

An aspect of the invention is a method of inhibiting the formation of fouling deposits occurring in spent caustic wash systems used for ethylene dichloride manufacturing processes which are in contact with ethylene dichloride processing streams contaminated with oxygen-containing compounds, which deposits are formed in ethylene dichloride processing streams contaminated with oxygen-containing compounds while in contact with a caustic solution having a pH>7, which comprises adding an effective deposit-inhibiting amount of a non-enolizable carbonyl compound to said caustic solution.

The non-enolizable carbonyl compound may be selected from the group consisting of formaldehyde, glyoxal, benzaldehyde, p-anisaldehyde, formic acid, glyoxalic acid and paraformaldehyde. The oxygen-containing compound may be a carbonyl compound. Moreover, the carbonyl compound may be acetaldehyde. For the practice of this invention, the non-enolizable carbonyl compound is added to the alkaline scrubber in an amount representing a molar ratio of non-enolizable carbonyl to carbonyl from about 25:1 to about 3:1. Preferably, the non-enolizable carbonyl compound is added to the alkaline scrubber in an amount representing a molar ratio of non-enolizable carbonyl to carbonyl from about 10:1 to about 3:1. Most preferably, the non-enolizable carbonyl compound is added to the alkaline scrubber in an amount representing a molar ratio of non-enolizable carbonyl to carbonyl from about 5:1 to about 3:1.

The inhibitors of the present invention can be added to the individual operational units as neat material or in solution form. A dilute solution may be preferred so that accurate metering of the inhibitor to the individual operating units can be achieved. Additionally, it is noted that the inhibitors of the present invention may be used in conjunction with other chemical treatments, such as anti-foams, corrosion inhibitors, anti-oxidants, dispersants metal deactivators and anti-polymerants.

The solvents suitable for use in diluting the inhibitors of the present invention include water, alcohol, hydrocarbon extraction systems, pyrolysis gasoline and generally any other solvents that are compatible with all or part of the medium in each process unit.

The solution should be added to the system in sufficient quantity to assure that the molar amount of inhibitor is effective to prevent fouling. Treatment ranges of from 1 to 10,000 ppm of inhibitor in the medium may be utilized if no convenient method of measuring carbonyl concentration is available. Where the carbonyl concentration is known or estimable, the inhibitor is preferably added in excess of the carbonyl equivalents.

As applied to treat a spent caustic wash system, the inhibitors may be added directly to the spent caustic wash system and/or any associated settling tank or stripper column.

The following examples are presented to describe preferred embodiments and utilities of the invention and are not meant to limit the invention unless otherwise stated in the claims appended hereto.

EXAMPLE 1

This experimental procedure was utilized for the qualitative analysis of formaldehyde. Potassium hydroxide (1M, 10 mL) was added to each of two tapered centrifuge tubes. Then, to one of the tubes was added formalin, which is 37 wt % formaldehyde in water, (250 mL, 3.1 mmoles formaldehyde). The tube was capped and shaken. Next, acetaldehyde (100 mL, 1.79 mmoles) was added to both tubes and the tubes were capped and shaken. The tubes were allowed to sit undisturbed for 1 week at room temperature.

After one week, a red-orange precipitate had settled from the blank tube (no non-enolizable carbonyl added). The tube dosed with formaldehyde contained no precipitate. The solution was slightly orange, but clear and translucent. Thus, formaldehyde effectively inhibited the formation and precipitation of polymeric foulant from the caustic solution.

EXAMPLE 2

Benzaldehyde and p-anisaldehyde were qualitatively analyzed according to the procedure described in Example 1, with slight modifications. Three tubes were utilized to perform the test: one blank, one treated with 250 mL of benzaldehyde, and one treated with 250 mL of p-anisaldehyde. The aldehydes were not miscible with the caustic solution. The tubes were shaken vigorously to emulsify the mixtures but two phases eventually settled out: a large caustic bottom phase and a small organic upper phase of aldehyde.

Nevertheless, after sitting overnight, the blank tube contained precipitated foulant but the tubes containing benzaldehyde and p-anisaldehyde remained clear and free of precipitate. This experiment shows that the aldehydes do not necessarily need to be miscible with caustic to inhibit polymerization of the acetaldehyde.

EXAMPLE 3

Glyoxal and paraformaldehyde were qualitatively analyzed in the following manner. Potassium hydroxide (1M, 10 mL) was added to each of three tapered centrifuge tubes. Then, paraformaldehyde (400 mg) was added to one of the tubes. To one of the other tubes was added a 40% solution of glyoxal in water (1.1 mL, ~8 mmol). The tubes were capped and shaken. Next, acetaldehyde (100 mL, 1.79 mmoles) was added to each tube and the tubes were capped and shaken vigorously.

After sitting undisturbed overnight at room temperature, 0.5 mL of orange solids had precipitated from the blank tube. The tubes treated with paraformaldehyde and glyoxal were free and clear of precipitate. The solutions were colorless and translucent.

EXAMPLE 4

A determination of the weight equivalents of paraformaldehyde required for inhibition of the caustic-catalyzed polymerization of acetaldehyde was made in the following manner. Paraformaldehyde was added to 10 vials as shown in Table I below. Potassium hydroxide (1M, 10 mL) was added to each of the ten scintillation vials plus a blank vial. The vials were capped and shaken vigorously until all of the paraformaldehyde was dissolved.

Next, acetaldehyde (79 mg) was added to each vial and the vials were capped and shaken. After sitting undisturbed overnight at room temperature, orange solids had precipitated from the blank vial and vials 1 and 3. Vial 2 was clear and contained no solids. Vials 4–10 were clear and free of polymer.

This test was repeated exactly as described except that a maximum of only five weight equivalents of paraformaldehyde was used. The results of this test showed that the blank and vial 1 contained precipitated orange solids. Vial 2 had developed a yellow color but contained no solids. Tubes 3–5 were clear and free of solids or color.

This test was repeated a third time and the appearance of the vials was evaluated after 3–4 hours instead of overnight. In this test, the blank and vial 1 contained precipitated orange solids. Vials 2 and 3 developed a pale yellow color but contained no solids. Tubes 4–5 were clear and free of solids or color.

The overall results show that only two weight equivalents of paraformaldehyde were required to prevent the precipitation of solids formed by the caustic-catalyzed polymerization of 1 weight equivalent of acetaldehyde.

TABLE I

| vial number | paraformaldehyde (mg) | equivalents per wt of acetaldehyde |
| --- | --- | --- |
| 0 | 0 | 0 |
| 1 | 80 | 1 |
| 2 | 160 | 2 |
| 3 | 240 | 3 |
| 4 | 320 | 4 |
| 5 | 400 | 5 |
| 6 | 480 | 6 |
| 7 | 560 | 7 |
| 8 | 640 | 8 |
| 9 | 720 | 9 |
| 10 | 800 | 10 |

EXAMPLE 5

The determination of the weight equivalents of glyoxal required for inhibition of the caustic-catalyzed polymerization of acetaldehyde was made in the following manner. Portions of a 40% glyoxal in water were added to 10 vials as shown in Table II below.

Potassium hydroxide (1M, 10 mL) was then added to each of the ten scintillation vials plus a blank vial. The vials were capped and shaken vigorously to completely mix the liquids. Next, acetaldehyde (79 mg) was added to each vial and the vials were capped and shaken.

After sitting undisturbed for 3–4 hours at room temperature, orange solids had precipitated from the blank vial and vials 1–6. The liquid in vials 1–6 was also slightly cloudy; the cloudiness decreased with increasing vial number (glyoxal content). Vials 7–10 were clear and free of polymer. The liquid in vial 7 was bright yellow. The color of the liquids in vials 8–10 was pale yellow, probably from the large concentration of glyoxal.

These results show that 14 weight equivalents of glyoxal were required to completely prevent the precipitation of solids formed by the caustic-catalyzed polymerization of 1 weight equivalent of acetaldehyde.

TABLE II

| vial number | glyoxal (mg) | equivalents per wt of acetaldehyde |
| --- | --- | --- |
| 0 | 0 | 0 |
| 1 | 124 | 2 |
| 2 | 248 | 4 |
| 3 | 372 | 6 |
| 4 | 496 | 8 |
| 5 | 620 | 10 |
| 6 | 744 | 12 |

TABLE II-continued

| vial number | glyoxal (mg) | equivalents per wt of acetaldehyde |
|---|---|---|
| 7 | 868 | 14 |
| 8 | 992 | 16 |
| 9 | 1116 | 18 |
| 10 | 1240 | 20 |

The above examples illustrate the utility of the antifoulant in a caustic solution. Since the same caustic environment is present in an ethylene dichloride caustic wash unit, these results show that the antifoulant can be successfully used as an anti-foulant during ethylene dichloride manufacture.

This invention has been described in relationship to ethylene dichloride units. Yet the method of this invention may also find applicability for the prevention of fouling during the processing of other halogenated hydrocarbons.

Changes can be made in the composition, operation and arrangement of the method of the present invention described herein without departing from the concept and scope of the invention as defined in the following claims:

We claim:

1. A method of inhibiting the formation of fouling deposits occurring in spent caustic wash systems used for ethylene dichloride manufacturing processes which are in contact with ethylene dichloride processing streams contaminated with oxygen-containing compounds, which deposits are formed in ethylene dichloride processing streams contaminated with oxygen-containing compounds while in contact with a caustic solution having a pH>7, which comprises adding an effective deposit-inhibiting amount of a non-enolizable carbonyl compound to said caustic solution.

2. The method of claim 1 wherein the non-enolizable carbonyl compound is selected from the group consisting of formaldehyde, glyoxal, benzaldehyde, p-anisaldehyde, formic acid, glyoxalic acid and paraformaldehyde.

3. The method of claim 2 wherein the oxygen-containing compounds are carbonyl compounds.

4. The method of claim 3 wherein the carbonyl compound is acetaldehyde.

5. The method of claim 3 wherein the non-enolizable carbonyl compound is added to the spent caustic wash system in an amount representing a molar ratio of non-enolizable carbonyl to carbonyl from about 25:1 to about 3:1.

6. The method of claim 3 wherein the non-enolizable carbonyl compound is added to the spent caustic wash system in an amount representing a molar ratio of non-enolizable carbonyl to carbonyl from about 10:1 to about 3:1.

7. The method of claim 3 wherein the non-enolizable carbonyl compound is added to the spent caustic wash system in an amount representing a molar ratio of non-enolizable carbonyl to carbonyl from about 5:1 to about 3:1.

* * * * *